United States Patent [19]

Kelen

[11] Patent Number: 4,883,065
[45] Date of Patent: Nov. 28, 1989

[54] MICROPOTENTIAL ANALYZER—A HOLTER SYSTEM WITH COMPREHENSIVE ANALYSIS CAPABILITY FOR VERY LOW AMPLITUDE ELECTROCARDIOGRAPHIC SIGNALS AND METHOD

[75] Inventor: George J. Kelen, Staten Island, N.Y.
[73] Assignee: Del Mar Avionics, Irvine, Calif.
[21] Appl. No.: 271,903
[22] Filed: Nov. 15, 1988
[51] Int. Cl.$^4$ ............................................... A61B 5/04
[52] U.S. Cl. ................................... 128/711; 128/696; 346/33 ME
[58] Field of Search ............... 128/710, 711, 712, 696; 316/33 ME

[56] References Cited

U.S. PATENT DOCUMENTS

| | | | |
|---|---|---|---|
| 4,098,267 | 7/1978 | Stein et al. | 128/712 |
| 4,333,475 | 6/1982 | Moreno et al. | 128/711 |
| 4,457,315 | 7/1984 | Bennish | 128/711 |
| 4,624,263 | 11/1986 | Salvin | 128/710 |
| 4,680,708 | 7/1987 | Ambos et al. | 128/702 |
| 4,696,306 | 9/1987 | Shiozaki | 128/710 |

Primary Examiner—Lee S. Cohen
Assistant Examiner—Scott M. Getzow
Attorney, Agent, or Firm—W. D. English

[57] ABSTRACT

A system for detection, measurement, analysis and plotting of electrocardiographic signals with amplitudes ranging down to one microvolt (micropotentials) employing long term ambulatory (Holter) recordings. Multi-channel electrocardiograms are recorded on a Holter recorder that inscribes calibration pulses at the beginning of each tape. The tape is played back at high speed on a scanner which uses the recorded calibration pulses to automatically calibrate the signal gains for each signal channel. The played back signals are digitized at sufficient resolution and sampling rate to permit analysis of micropotentials. The digitized raw data is stored in a permanent computer file available for multiple further analyses. A template heart beat is designated and the raw data file is signal averaged to reduce random noise. The averaged beat thus produced is permanently stored, and analyzed using a variety of operator selected standard signal processing techniques to reveal and evaluate micropotential signals of clinical significance.

12 Claims, 5 Drawing Sheets

MICROPOTENTIAL ANALYZER—A HOLTER SYSTEM WITH COMPREHENSIVE ANALYSIS CAPABILITY FOR VERY LOW AMPLITUDE ELECTROCARDIOGRAPHIC SIGNALS AND METHOD

BACKGROUND OF THE INVENTION

This invention relates generally to the field of electroncardiography and specifically to the area of long term ambulator electrocardiography generally referred to as Holter monitoring. The invention teaches a means for extending the application of conventional Holter monitoring to permit the detection and characterization of very low amplitude signals in the microvolt range which contain important clinical information not discernible from Holter apparatus of any prior art.

Examples of very low amplitude electrocardiographic signals known to be of clinical importance include so called "Late Potentials" which occur at the terminal end of the QRS complex of the ECG and indicate a vulnerability to malignant ventricular arrhythmia, as well as HIS bundle potentials whose temporal relationship to the preceding atrial and succeeding ventricular signals allow important determinations to be made as to the functional integrity of the conduction system of the heart. The investigation of other potentially useful correlates of very low amplitude ECG signals is currently a subject of intensive basic and clinical research.

THE PRIOR ART

In orthodox Holter monitoring a patient wears a miniaturized recorder attached by wires and electrodes to the body surface to record (usually on magnetic tape) for an extended period of time (often 24 hours) the electrocardiographic signals generated by the heart's activity. The recording is later played back and analyzed using apparatus called a "scanner". During scanning the tape is played back at many times the speed at which it was recorded (typically 120 to 240 times as fast) while computerized logic in the scanner assists the operator in locating, counting and classifying abnormal electrocardiographic events or features.

The usual purpose of performing a conventional Holter recording and analysis is to discover and quantify intermittent events such as premature beats, paroxysms of abnormal heart activity or transient morphological changes in the electrocardiographic signals which may indicate temporary inadequacy of blood supply to the heart muscle ("silent ischemia"). Conventional Holter monitoring is concerned with cardiac signals whose amplitude is about a millivolt, in the presence of background noise of about 20 to 50 microvolts. Thus it cannot distinguish micropotential signals as they are of an amplitude less than the background noise level.

Outside the sphere of Holter monitoring, a variety of techniques have been used to analyze low amplitude electrocardiographic signals. Prior to this invention, these have employed "real-time" techniques by which apparatus is connected to a patient for a finite period of time, typically less than fifteen minutes, during which the machine makes an analysis according to a predetermined algorithm. Such equipment does not record the ECG raw data but rather processes it "on line", so that only the specific predetermined type of analysis for which the apparatus was intended and designed can be carried out. If a different analysis algorithm is desired, the patient must be reconnected to the apparatus and the whole study repeated. Some signal processing techniques known to be useful for the discovery and characterization of low amplitude electrocardiographic signals include (but are not limited to):

Magnification
Rectification
Vector summation
Filtering by a variety of techniques
Root mean square amplitude calculation The currently most useful technique for signal to noise ratio improvement is "signal averaging".

Real-time systems for study of low amplitude ECG phenomena have implemented various combinations of the above signal processing modes, usually in a narrowly and explicitly predefined manner for the explicit purpose of evaluating a specific phenomenon such as "Late Potentials".

BENEFITS OF THE INVENTION

The present invention teaches the detection and analysis of clinically important electrocardiographic signals of amplitudes a thousand times smaller than can be analyzed by conventional Holter systems. This invention also teaches separation of the data acquisition from the noise reduction and signal analysis phases of realtime micropotential analysis, by first permanently recording the signals on tape and then playing them back at high speed. Permanent storage of raw data signals permits their later reanalysis by a wide variety of algorithms. This invention further teaches a technique whereby a patient having Holter monitoring performed for any reason can prospectively or retrospectively be evaluated for clinically relevant micropotentials without the need to be hooked up to another piece of apparatus.

Thus in contrast to the prior art taught by conventional Holter monitoring systems which cannot resolve signals in the microvolt range, and real-time signal averaging and analysis systems which are restricted to a single fixed algorithmic analysis in real-time of patient ECG activity spanning a few minutes, the present invention teaches a method that allows for multiple analyses by an infinite variety of user determined algorithms of the same multi-channel raw patient ECG spanning a period of many hours.

The combination of analysis capability by a multitude of user-definable algorithms performed ad lib and "off line" on permanently recorded raw data spanning 24 hours confers several new, important and unique benefits:

Intermittently occurring low amplitude events may be studied.
One scanner can be used to analyze data collected on many inexpensive recorders.
Old raw data can be retrospectively reanalyzed whenever a new or better processing algorithm is discovered.

Probably the most significant benefit from this invention however, is the ability to perform micropotential analyses on Holter tapes recorded originally for conventional purposes. For example, the finding of a high grade ventricular arrhythmia can result in the immediate analysis of the same tape for presence of late potentials which would help classify the patient into a high or low risk group, without requiring the patient to "take another test".

SUMMARY OF THE INVENTION

The objective of this invention is to provide a system with all the elements necessary for:

The recording of multi-channel electrocardiographic signals on a long term ambulatory tape recorder, Provision of automatic amplitude calibration of signals during recording and subsequent playback (scanning), Digitization of the played back signals with adequate resolution (12 bits) and sampling frequency (>500 Hz) during scanning at 120× recording speed thus rapidly and conveniently providing signals of sufficient resolution and accuracy as to be suitable for later evaluation of micropotentials, Permanent disk storage of sufficient continuous digitized raw data to be suitable for signal averaging and analysis (typically 3 megabytes or 15 minutes of real time signal), Signal averaging for noise reduction, Signal display, measurement, manipulation and processing by a wide variety of mathematical and analytical techniques useful in evaluation of micropotentials, Hard copy and clinical report generation.

Integration of the above into a package with a user interface that is simple yet flexible.

The accompanying drawings depict these elements and the manner of their integration by which the system of the invention achieves its objectives, wherein.

DESCRIPTION OF THE PREFERRED EMBODIMENT

Figure 3:
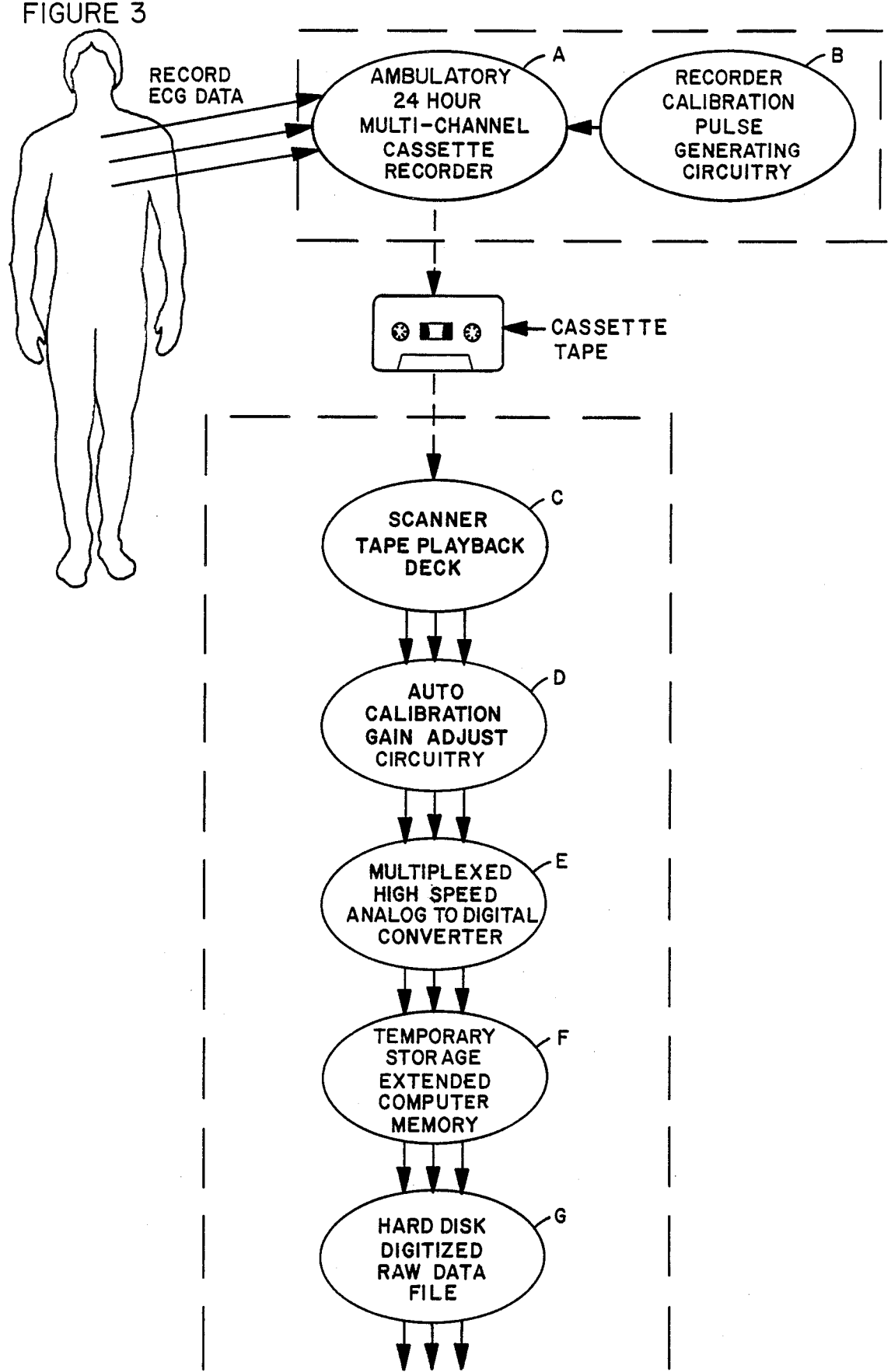
FIG. 3 shows the electrocardiographic signal path from patient through Holter recorder, tape playback scanner, automatic gain calibration system, analog to digital converter, and computer memory to generation of a permanent digitized raw data file.
Figure 4:
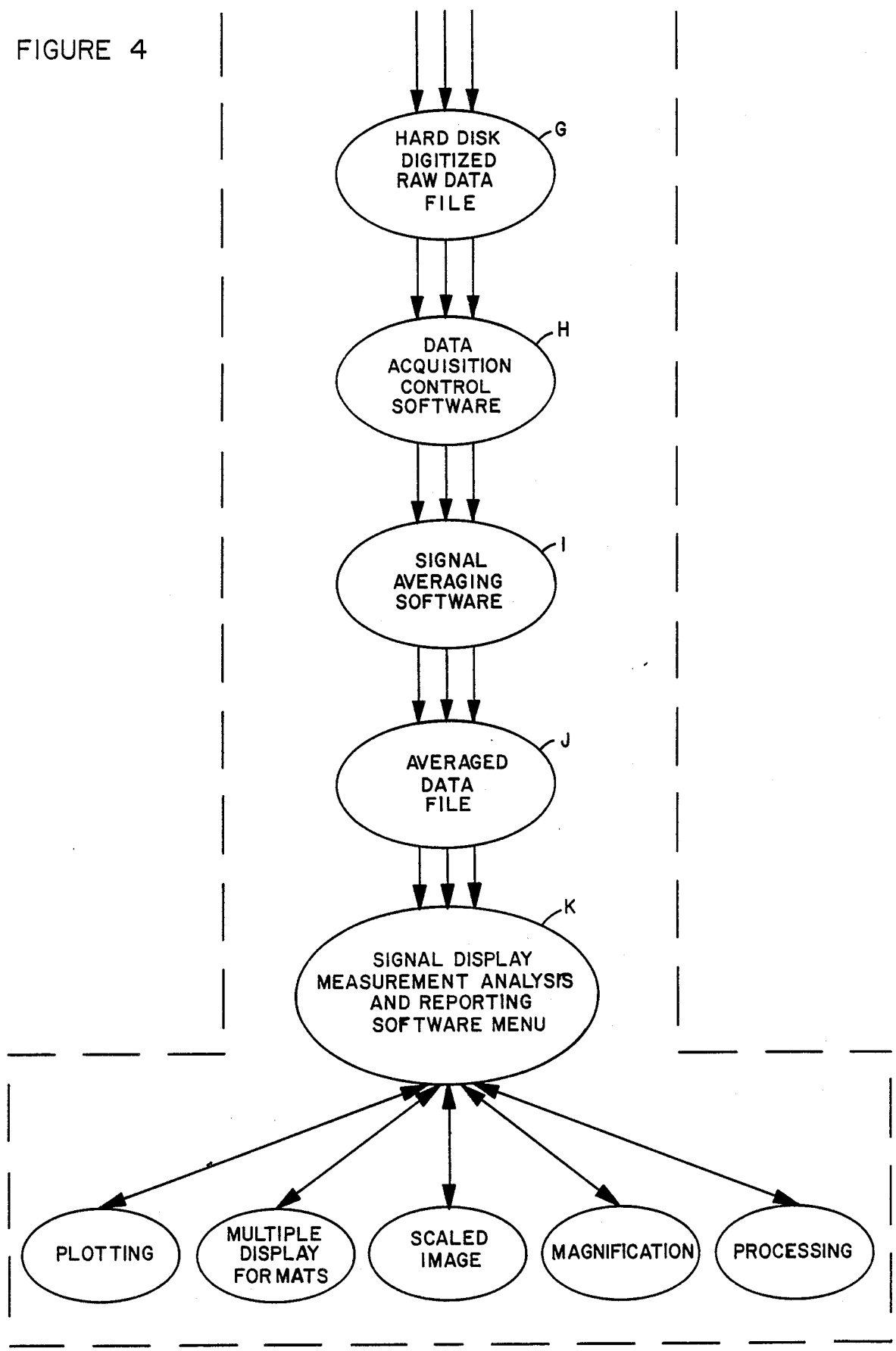
FIG. 4 illustrates the signal path from digitized raw data file through the noise reduction process of signal averaging to yield an averaged data file which may then be interactively used by the operator for the purposes of signal display, measurement, plotting or further processing.

For descriptive purposes, the system is divided into the following major functional elements as depicted in FIGS. 3 and 4

A Ambulatory 24 hour multi-channel recorder
B Recorder calibration pulse generation circuitry
C Tape playback deck operating at 120× recording speed (scanner)
D Auto-calibration gain adjust circuitry
E High speed high speed resolution Analog to digital conversion
F Temporary storage memory (extended computer memory)
G Digitized raw data file stored on hard disk
H Data acquisition control software
I Signal averaging software
J Averaged data file
K Signal display, measurement, analysis and reporting software menu The scanning, signal averaging, and analysis software is modular such that the operator may move freely within and between modules by appropriate menu keystroke selections. On screen prompts and appropriate help messages are liberally displayed on the CRT.

The function of each system element will now be described separately:

A AMBULATORY MULTICHANNEL TAPE RECORDER

Figure 1:
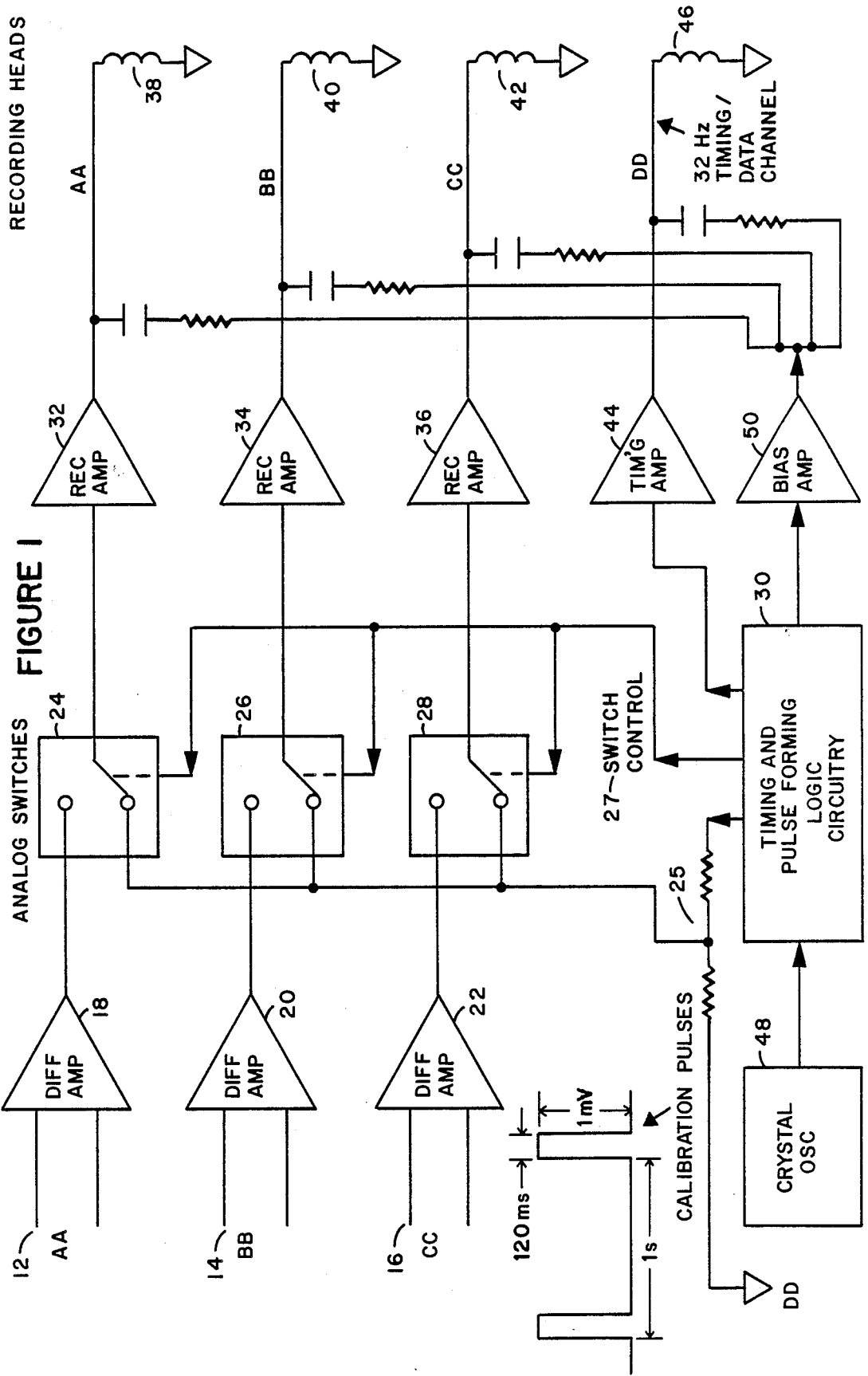
FIG. 1 is a block diagram of a multi-channel Holter recorder disclosing the means by which calibration pulses are recorded at the beginning of each tape.

A block diagram of a Holter recorder of the type used in the invention is disclosed in FIG. 1. Three channel capability is necessary for certain (but not all) algorithms used for micropotential analysis. The tape recorder employs three channels AA, BB, and CC with a 5.38 gain of electrocardiogram information and one timing channel DD. The recorder is worn on a belt or strap and is connected by cable conductors 12. 14 and 16 to skin electrodes applied at appropriate positions on the torso.

The Holter recorder shown in FIG. 1 includes three input differential amplifiers 18, 20 and 22 which are connected to respective input leads 12, 14 and 16 on which the three channels of electrocardiogram information appears. Amplifiers 18, 20 and 22 are connected through respective analog switches 24, 26 and 28 to recording amplifiers 32, 34 and 36. The recording amplifiers in turn are connected to respective recording heads 38, 40 and 42.

B RECORDER CALIBRATION PULSE GENERATION CIRCUITRY

For six minutes at the commencement of each recording, accurate calibration pulses of amplitude 1 millivolt (mV) and duration of 120 milliseconds (ms) occurring once every second (s) are switched into the inputs of the recording amplifiers 32, 34, 36 in lieu of the patient signals, by analog switches 24, 26, 28. The calibration pulses are derived from timing and pulse forming logic circuitry 30 driven by a crystal controlled oscillator 48, and a standardized voltage reference source.

Figure 2:
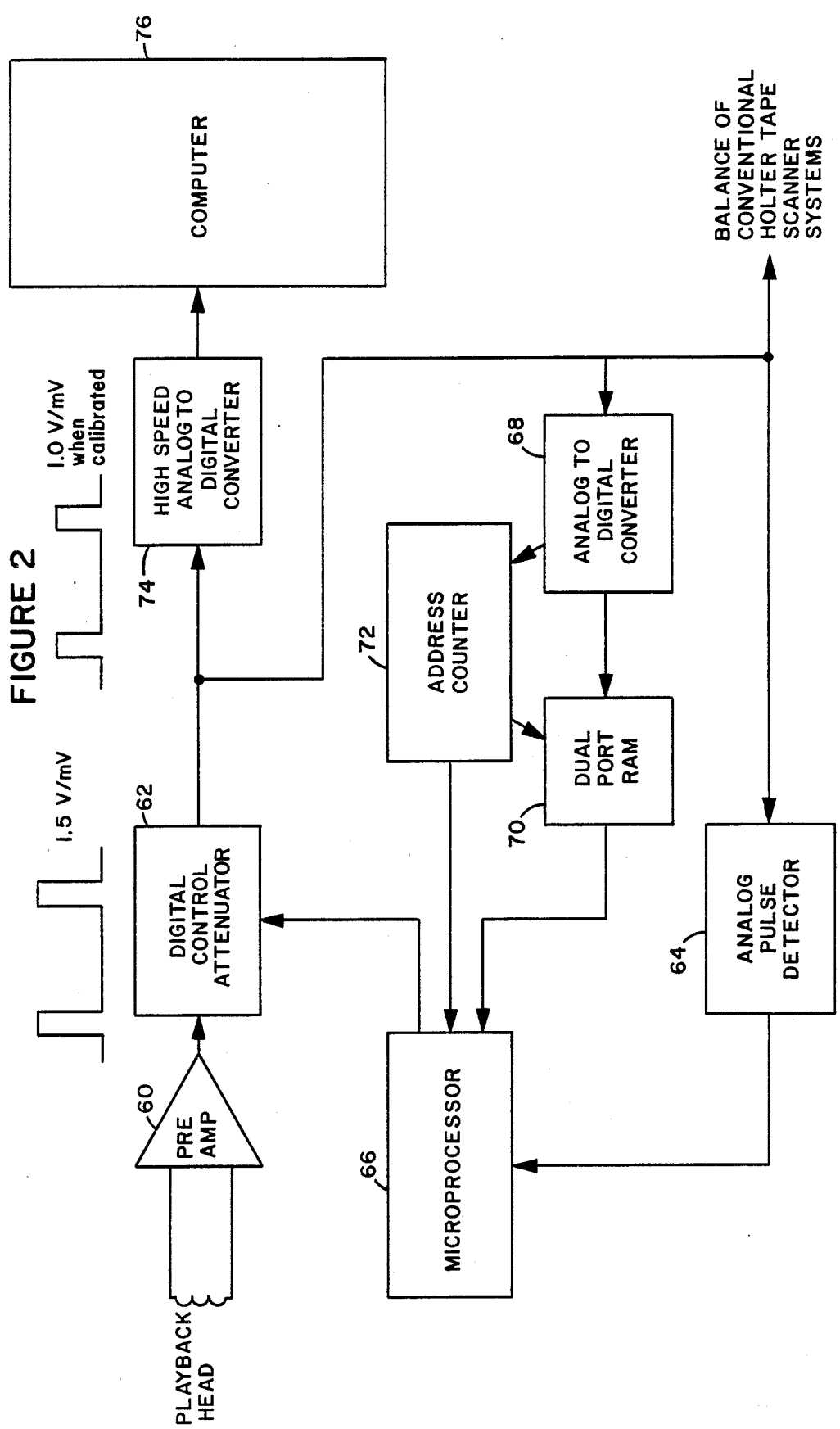
FIG. 2 is a block diagram showing a tape playback scanner, automatic calibration system and signal path through high speed analog digital conversion to a computer.

The recorder calibration pulse generation circuitry of FIG. 2 also includes a bias amplifier 50 connected to logic circuitry 30, and having output leads coupled through appropriate resistance/capacitance filters to the recording heads 38, 40 and 42. The recording heads produce three separate ECG channels on jthe tape of the tape recorder.

Logic circuitry 30 is also connected to a further recording amplifier 44 which, in turn, is connected to a recording head 46. Bias amplifier 50 is also coupled to recording head 46 through an appropriate resistance/capacitance filter. Recording head 46 provides a 32 Hz timing/data channel on the tape.

C TAPE PLAYBACK SYSTEM (SCANNER)

The resolution and sampling rates employed in typical conventional Holter scanners whilst adequate for arrhythmia analysis or silent ischemia monitoring, are inadequate for accurate depiction of very low amplitude signals. Moreover it is vital to preserve as much high frequency content and fidelity of the original signal as possible, whilst minimizing any additional noise due to the recording and playback processes. It is therefore necessary to provide a completely separate signal path from tape playback heads to the analog to digital converter, independent of that used for any conventional analysis. Moreover, it is vital that the gain of the signals used for micropotential be accurately calibrated. These functions are automatically accomplished in our playback system disclosed in FIG. 2 and are at the core of achieving the objects of the invention.

The playback scanner system of FIG. 2 includes a preamplifier 60 which is coupled to the playback head of one channel of the tape recorder of FIG. 1. It is to be understood that similar preamplifiers are coupled to the other playback heads.

Preamplifier 60 is coupled through an attenuator 62 to a high speed analog-digital converter 74 which is included in a computer 76.

The output of attenuator 62 is also introduced to an analog-digital converter 68 (which operates upon a dual port RAM 70, and an address counter 72), and to an analog pulse detector 64. Analog pulse detector 64 is connected to a microprocessor 66 which is operated upon by address counter 72 and dual port RAM 70 to provide a digital control for attenuator 62.

D AUTOMATIC PLAYBACK GAIN CALIBRATION

Automatic gain calibration is accomplished during scanning of the first six minutes of each tape as follows.

Referring again to FIG. 2, the gain of preamplifier 60 is initially set to provide a nominal gain of 1.5, so that a calibrated 1 millivolt at its input is 1.5 millivolts at the output of preamplifier 60, thus allowing for up to 30% amplitude margin on playback at point S1.

The signal is next passed through a digitally controlled attenuator 62 and then to the high speed analog-digital converter 74 in computer 76. Two simultaneous paths take the signal to analog pulse detector 64, which signals a microprocessor 66 whenever a recorded calibration pulse is found. A second simultaneous path passes through an analog to digital converter 68, whose output is written into a dual port random access memory 70. A continuously recycling address counter 72 provides input addresses. When pulse detector 64 signals processor 66 that a calibration pulse is present, processor 66 takes the address from counter 72 and measures pulse characteristics found at that memory location. Memory is continuously updated during this process but is large enough to allow measurements before new data overlays old. If the pulses found have incorrect characteristics of amplitude or shape, a new value is written to attenuator 62 to lower its output level. This process is repeated until correct values are set and verified for each data channel.

E. ANALOG TO DIGITAL CONVERSION

To provide a permanent record of the raw signal data suitable for micropotential analysis, the calibrated gain adjusted signals coming from the tape playback heads are continuously digitized by high speed analog-digital converter with 12 bit resolution at a sampling rate of 694 Hz per channel during playback at 120× recording speed. The high speed analog-digital converter 74 uses direct memory access to achieve a total throughput of 250,000 samples per second. It should be noted that this analog to digital conversion by analog-digital converter 47 is distinct and separate from that used in the autocalibration process described in D above.

F. TEMPORARY STORAGE IN VOLATILE MEMORY

Continuous data from E above, representing several hundred heart beats are stored initially in a random access memory in computer 76 using interrupt driven direct memory access from step E above. This is necessary because the analog-digital converter 74 needs to function at speeds so high that immediate storage on disk is not readily achievable at reasonable cost.

G. DIGITIZED RAW DATA FILE ON HARD DISK

At the conclusion of digitization, the raw data file is transferred from the random access memory of F above to a hard disk file, along with gain and timing calibration data as well as biographical and clinical data about the patient entered by the operator.

H. DATA ACQUISITION CONTROL SOFTWARE

In our preferred embodiment, the micropotential analysis system is integrated within a Holter scanning system that is also suitable for conventional arrhythmia and silent ischemia analysis, which are normally performed from the same tape prior to commencing micropotential analysis.

Control by the operator is achieved through an alphanumeric keyboard as well as by use of a mouse. Data in the form of signal displays with textual and numeric annotation is displayed on a color CRT, whilst hard copy is generated on a laser printer whenever desired. At each point in the micropotential analysis process, available choices are presented on a menu at the bottom of the CRT screen, with the suggested next step highlighted.

During the process of conventional scanning for arrhythmias, the operator notes the time(s) at which micropotential analysis will later be performed. This would normally be during a period of rest or sleep when the ECG signals should be most free from noise and artefact.

Upon entry to the micropotential system, any biographical or clinical patient data already entered by the operator during conventional arrhythmia scanning is automatically transferred to and maintained by the micropotential software. The operator is now prompted to enter the file name under which the micropotential data will be stored, the start time and duration for which the tape signals are to be digitized for later micropotential analysis. Any number of such digitized raw data files may be generated from various time samples of a single tape. The software now causes the tape playback transport to seek and find the segment of tape requested and commences to play the tape from that point whilst simultaneously displaying the signals on the CRT. The operator is now prompted to adjust the gain of the A/D converter by pressing keys so that the signals displayed just fill the display window but do not saturate. This step is provided to optimize the dynamic range spanned by the A/D converter 74 and maximize signal resolution. When the operator has signalled completion of gain adjustment by hitting another key, the tape is repositioned to the start of the desired data segment and the operator prompted to commence data acquisition. At the conclusion of digitization of the desired data segment, the digitized raw data file F is automatically stored on hard disk G and the operator prompted to proceed to the usual next step of signal averaging I, or some other activity may optionally be selected such as immediate acquisition of data from a different segment of the tape for later analysis. The software also automatically tests for sufficient disk storage space and allows for housekeeping activities such as file directory searches, file deletion and optional archiving to streaming tape.

I. SIGNAL AVERAGING SOFTWARE

Signal averaging for noise reduction is accomplished on raw digitized data files generated in the manner described above. The software aligns each successive heart beat in the file to a "template" beat indicated by the operator, rejects it if it does not conform within operator defined limits, and otherwise sums it with the previously accepted beats. After the last beat, the summed value for each data point is divided by the number of beats accepted to yield an average value for each data point from all the beats accepted. Because noise is by definition randomly occurring, whilst signal events have a fixed timing relationship to each other, noise cancels itself out whilst true signal components become augmented. Noise is reduced by the square root of the number of beats averaged—a tenfold noise reduction results from averaging 100 beats.

A single raw digitized data file may contain examples of several different beat families, for example extrasystoles or bigeminal rhythms in which "normal" and "abnormal" heart beats alternate. Unlike real-time systems, ours allows separate averaging and analysis of multiple beat morphologies from a single raw data segment, since the raw data is always available for reuse. Moreover the operator is at liberty to indicate which beat morphology is to be designated the template, and how closely each beat must resemble that template in order to be accepted into the average.

Upon menu selection of the signal averaging activity, the most recently acquired raw data file is automatically loaded and displayed on the CRT. The operator may scroll backwards and forwards through the file until a beat to be used as the template is found. Using the mouse, this beat is then positioned to the center of the display window, and the region to be used for alignment and correlation with later beats indicated using the mouse buttons. The operator may indicate that only certain channels are to be used for beat acceptance determination if some signal channels are unacceptably noisy. The operator then presses a key to commence the averaging process, during which the currently computed average beat is displayed every few beats, as well as the number of beats so far accepted, the number rejected as too noisy and current file position. The operator may at any time interrupt the averaging activity to select a new template or modify the correlation criterion for beat acceptance. At the conclusion of the averaging process, the operator is prompted to proceed to another activity, usually signal analysis and report generation.

J. AVERAGED DATA FILE

At the end of the signal averaging process described above, the averaged signal together with all biographical and clinical patient data are written to a file on hard disk for later analysis. Since this file is permanent, it may be re-analyzed by different algorithms at any time without a need to reaccess the patient, rescan the tape, or even reperform the signal averaging step.

K SIGNAL DISPLAY, MEASUREMENT, ANALYSIS AND REPORTING SOFTWARE

Upon entry to this software module, the most recently written averaged data file is automatically loaded and displayed on the CRT.

This software module provides the functionality of an intelligent digital oscilloscope, allowing the operator to choose from among a very wide variety of signal display, manipulation, measurement, calculation, computation and report generation options. Regions of signal interest are generally identified by pointing to them with the mouse, whilst the next desired step is selected by menu keystroke.

The various signal processing steps can be sequentially selected by the operator in any order, whilst certain commonly used complex sequences, such as may be useful in the measurement of late potentials or HIS potentials, are accessible through a single preprogrammed keystroke. At any time during an analysis sequence, the operator may restore the original raw data or obtain a hard copy printout. The system can also generate a report suitable for clinical use.

The operator may choose to perform a processing step on a single signal channel or all channels simultaneously. Signal channels may be combined in certain ways, filtered by several different methods or complex computations performed on regions of signal interest.

Indicated portions of signal be magnified both vertically and horizontally using the mouse, for detailed examination of microvolt amplitude signals. Any signal display format available on the CRT can also be plotted on the laser printer. Amplitude and time measurements between current cursor positions (which are mouse manipulated) are automatically and continuously displayed on the CRT.

Figure 5:
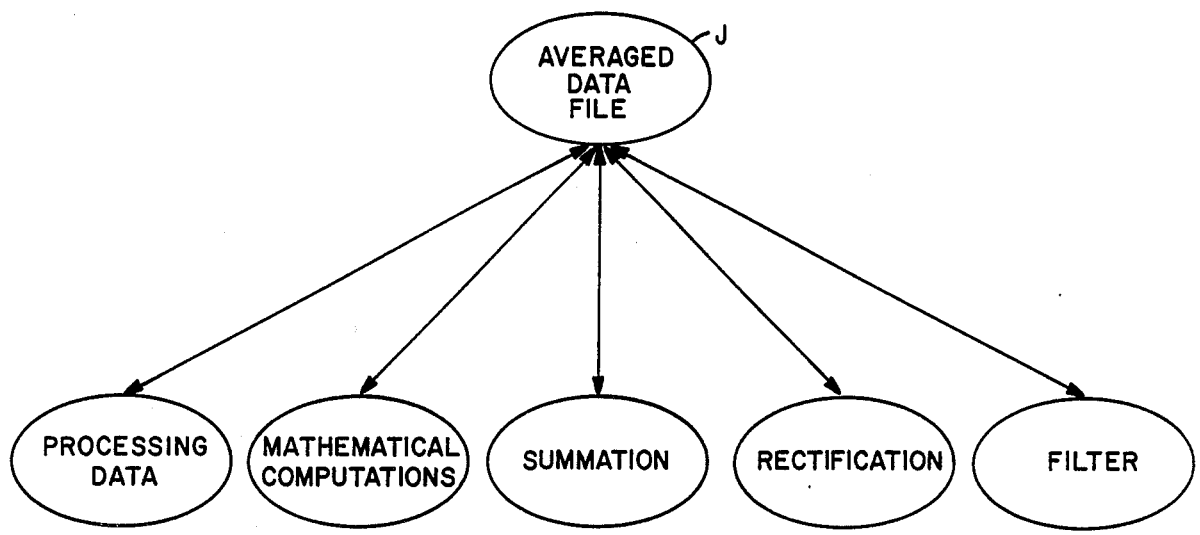
FIG. 5 depicts some specific complex operations which the user may apply to the averaged data file to further elucidate micropotential characteristics.

Available activity options such as shown in FIG. 5 which is always available to the operator by pressing a single key. These include Rectification
Inversion
Root mean square amplitude calculation
Delineation of QRS complex onset and offset
Butterworth bandpass filtering in forward, reverse or bidirectional modes, with operator selection of upper and lower corner frequencies
FFT variable order bandpass filtering
Vector summation of three channels
Identification of isoelectric line
Measurement of late potential parameters An analysis session may terminate by generation of a report or return to another micropotential related activity such as acquisition of data from a different portion of the same tape, re-averaging of an already stored raw data file, or return to conventional arrhythmia scanning of another tape.

We claim:

1. A micropotential analyzer system for long term ambulatory multi channel recording, high speed playback and analysis of electrocardiographic (ECG) signals ranging in amplitude down to one microvolt, said system including: a multi channel magnetic tape Holter recorder; micropotential analyzing means coupled to the recorder for allowing a user to select from an entire recording on the recorder a precise segment of raw data that is to be the subject of micropotential analysis thereby permitting analysis of multiple data segments from a single tape on the recorder and reanalysis of any raw data set by multiple processing algorithms; and recording means coupled to said recorder for recording data on said recorder and further incorporating circuitry which records on each signal channel on said recorder a calibration signal of precisely known shape and amplitude on a portion of the recording in each such signal channel.

2. The system of claim 1, and which includes playback means for the signals recorded on said recorder and further incorporating calibration circuitry to measure the played back amplitude of the calibration signals recorded on the signal channels of said recorder and responsive to said calibration signals to adjust the overall gain of said playback means such that precisely calibrated measurements of said ECG signals recorded on said recorder can be made by said analyzing means.

3. The system defined in claim 2 and in which said playback plays back recorded ECG signals from said recorder at precisely calibrated speeds many times greater than that at which said ECG signals were recorded.

4. The system defined in claim 2, in which said analyzing means includes circuit means for performing continuous analog to digital conversion of said ECG signals generated by said playback means with sufficient precision to resolve micropotentials of 2 microvolts amplitude on multiple channels at a sampling rate equivalent to at least 500 Hz real time, suitable for evaluating signals of clinical relevance.

5. The system defined in claim 4 in which said analog to digital converting means further generates digitized data calibrated in amplitude and timing for recording in digital format on permanent media and processing by said analyzing means.

6. The system defined in claim 5, in which said analyzing mean incorporates means for generating video display signals, automatically calibrated measurement signals, annotation signals, hard copy signals, and signals for the manipulation of digitized data generated by said analog to digital conversion means under control and selection of an operator performing an analysis.

7. The system of claim 6 and which includes video display means and control means therefor having the further ability to magnify or zoom in both axes, with automatic scaling, portions of a recorded ECG signal interactively designated by said operator.

8. The system of claim 6 and calibration means therefor having the further property of being automatically applied to any portion of recorded ECG signals interactively designated by said operator.

9. The system of claim 6 and which includes manipulation means for further implementing general purpose signal processing algorithms useful in the elucidation of micropotentials, such as signal averaging for noise reduction, digital filtering of several types, rectification, scaling vector summation and root mean square amplitude calculation.

10. The system of claim 9, in which the manipulation means includes processing steps user-selectable from menus, either singly or in predefined sequential combination for performance of specific complex analyses.

11. The system of claim 6 and which includes hard copy generation means having the capability for generating a paper facsimile of any display generated by said analyzing means including results of complex multi-step analyses.

12. A computer based process for analyzing low amplitude micropotentials off Holter recorded electrocardiographic signals, comprising the steps of:
recording at least one calibration pulse(s) in at least one Holter recording medium;
Holter recording at least one orientation (view or channel) of electrophysiological data in said
Holter recording medium; automatically calibrating a high speed recorded data scanning system with said recorded calibration pulse(s);
searching said recorded electrophysiological data with said scanning system and selecting a continuum of data for micropotential analysis;
excerpting and analog to digital converting of said data continuum with resolution suitable for micropotential analysis;
storing said digitized data continuum initially in computer memory with subsequent permanent storage in digital format;
designating a particular electrophysiological periodic wave function within said stored data continuum as a template with defined parameters to which all other periodic wave functions within said continuum may be compared;
aligning and comparing all periodic wave functions stored in said continuum with said template;
rejecting from further signal processing all said compared periodic wave functions that do not match said template within a predefined correlation;
accepting for further signal processing all said compared periodic wave functions that do correlate within acceptance limits of said template;
averaging all said accepted periodic wave functions;
storing said averaged periodic wave function in a permanent file in digital format;
subjecting said stored, averaged periodic wave functions to further operator designated signal processing for micropotential analysis by any or all of the following:
visual examination and automatic measurement of user designated signal portions;
magnification of user designated signal portions in either or both axes;
digital filtering of various types;
rectification;
vector summation;
scaling;
root mean square amplitude calculation;
paper facsimile and report generation.

* * * * *